(12) United States Patent
Ellman et al.

(10) Patent No.: US 7,294,116 B1
(45) Date of Patent: *Nov. 13, 2007

(54) SURGICAL SMOKE PLUME EVACUATION SYSTEM

(76) Inventors: Alan G. Ellman, 3333 Royal Ave., Oceanside, NY (US) 11572; Jon C. Garito, 3333 Royal Ave., Oceanside, NY (US) 11572

( * ) Notice: Subject to any disclaimer, the term of this patent is extended or adjusted under 35 U.S.C. 154(b) by 223 days.

This patent is subject to a terminal disclaimer.

(21) Appl. No.: 11/027,610

(22) Filed: Jan. 3, 2005

(51) Int. Cl.
*A61N 1/30* (2006.01)

(52) U.S. Cl. .............................. 604/19; 604/20; 604/21; 604/22; 604/23; 604/24; 604/25; 604/26; 604/27; 24/144; 24/170

(58) Field of Classification Search .................. 604/19, 604/20–22, 23–26, 27
See application file for complete search history.

(56) References Cited

U.S. PATENT DOCUMENTS

| | | | | |
|---|---|---|---|---|
| 5,047,072 A | * | 9/1991 | Wertz et al. ................... | 95/90 |
| 5,055,100 A | * | 10/1991 | Olsen ........................... | 604/22 |
| 5,160,334 A | * | 11/1992 | Billings et al. ................ | 606/34 |
| 5,709,675 A | * | 1/1998 | Williams ........................ | 606/1 |
| 6,001,077 A | * | 12/1999 | Ellman et al. ................. | 604/35 |
| 6,685,665 B2 | * | 2/2004 | Booth et al. ................... | 604/26 |

* cited by examiner

*Primary Examiner*—Tatyana Zalukaeva
*Assistant Examiner*—Ginger T. Chapman (57) ABSTRACT

Smoke evacuation apparatus designed to provide safe and efficient filtration and evacuation of smoke plume generated by laser-surgical, electrosurgical, radiosurgical, and electrocautery devices. A filter assembly is removably mounted on a front panel of the apparatus housing and is thus easily accessible from the front side which typically faces the user. The filter assembly at its front is provided with a hose connector to which the suction hose of the system is conveniently attached, and the front of the filter assembly is configured with a symbol, such as a letter or number, that represents an identification of the system supplier or manufacturer, and the hose connector is mounted on that symbol identifier.

17 Claims, 7 Drawing Sheets

SURGICAL SMOKE PLUME EVACUATION SYSTEM

The invention is directed to apparatus designed to provide safe and efficient filtration of smoke plume generated by laser-surgical, electrosurgical, radiosurgical, cautery, hyfrecators and electrocautery devices.

BACKGROUND OF INVENTION

Surgical smoke evacuation systems are designed to capture the smoke and plume generated during surgical procedures in which there is thermal destruction of tissue or bone. The plume from vaporized tissue contains small particles and gases that could be potentially hazardous. If not evacuated the materials can become airborne and deposit in the respiratory tracts of the surgical team. The type of surgical instruments, the characteristics of tissue, and the surgeon=s technique affect the quantity and characteristics of the smoke plume. A surgical smoke evacuator is in essence a vacuum pump, usually footswitch operated, that incorporates one or more filters to remove particles from the suctioned air-stream at the surgical site. A hose, typically of plastic, disposable or reusable, connects the pump to a disposable or autoclavable wand serving as a nozzle that is usually held about 5 cm. from the tissue to remove smoke generated by the surgical procedure. Because the constraints of some surgical procedures can prevent placement of the nozzle close to the tissue, smoke evacuators should capture smoke effectively at up to 15 cm. Adequate protection from potentially dangerous smoke plume can only be achieved when the plume is successfully captured before it comes into contact with the patient and surgical staff. This smoke entrainment requires that the evacuator airflow change the smoke direction and draw it into the hose via the wand.

An example of a smoke evacuation system is described in our U.S. Pat. No. 6,001,077, the contents of which are herein incorporated by reference, and is commercially-available from Ellman International, Inc. of Oceanside, N.Y. This system features a viral paper filter in the suction hose and a charcoal filter inside the system housing. Changing the hose filter requires disassembling the hose and removing and disposing of the filter assembly, and reinstalling a fresh filter. Changing the charcoal filter requires opening of the housing, removing the filter bowl for the filter, and replacing the spent filter with a new filter and reassembling. This can be unnecessarily time consuming.

SUMMARY OF INVENTION

A principal object of the invention is surgical smoke evacuation apparatus that overcomes one or more of the drawbacks listed above.

This and other objects of the invention are achieved in accordance with one feature of the invention by provision of a smoke evacuation system wherein the filter assembly is mounted in the form of a unitary body, such as a cartridge, on a housing panel, and is easily removed and replaced as a unitary body by the user grasping the filter assembly where it is accessible from the outside, pulling it out from its position on the housing, and replacing the entire filter assembly as a unit without having to contact the filter elements.

In accordance with a further feature of the invention, the filter assembly is removably mounted on a front panel of the housing and is thus easily accessible from the front side which typically faces the user.

In accordance with still another feature of the invention, the filter assembly at its front is provided with a hose connector to which the suction hose of the system is conveniently attached. A further feature is to configure the front of the filter assembly with a symbol, such as a letter or number, that represents an identification of the system supplier or manufacturer, and mounting the hose connector on that symbol identifier. Preferably, the symbol is in 3-dimensions (3-D) so it stands out from the unit.

As still another feature, the symbol identifier is configured to serve as a handle to simplify a user grasping the filter assembly during the removal step.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

SUMMARY OF THE DRAWINGS

In the drawings:

FIG. 6 is an interior partly cross-sectional view of the filter cartridge identifying its filter components;

DETAILED DESCRIPTION OF PREFERRED EMBODIMENTS

The above-identified patent, whose contents have been incorporated by reference, describes surgical smoke evacuation apparatus that employs two spaced independent filters in series in the suction path. The first filter is a viral pre-filter in the hose which is capable of filtering micro-organisms bigger than 0.02 microns in size. Following the pre-filter is a charcoal filter in the housing that efficiently removes odors. The construction of the latter has in common with that of the invention a housing for a vacuum blower optionally with a muffler coupled to the interior filter. The inlet connection is by a hose.

Figure 1:
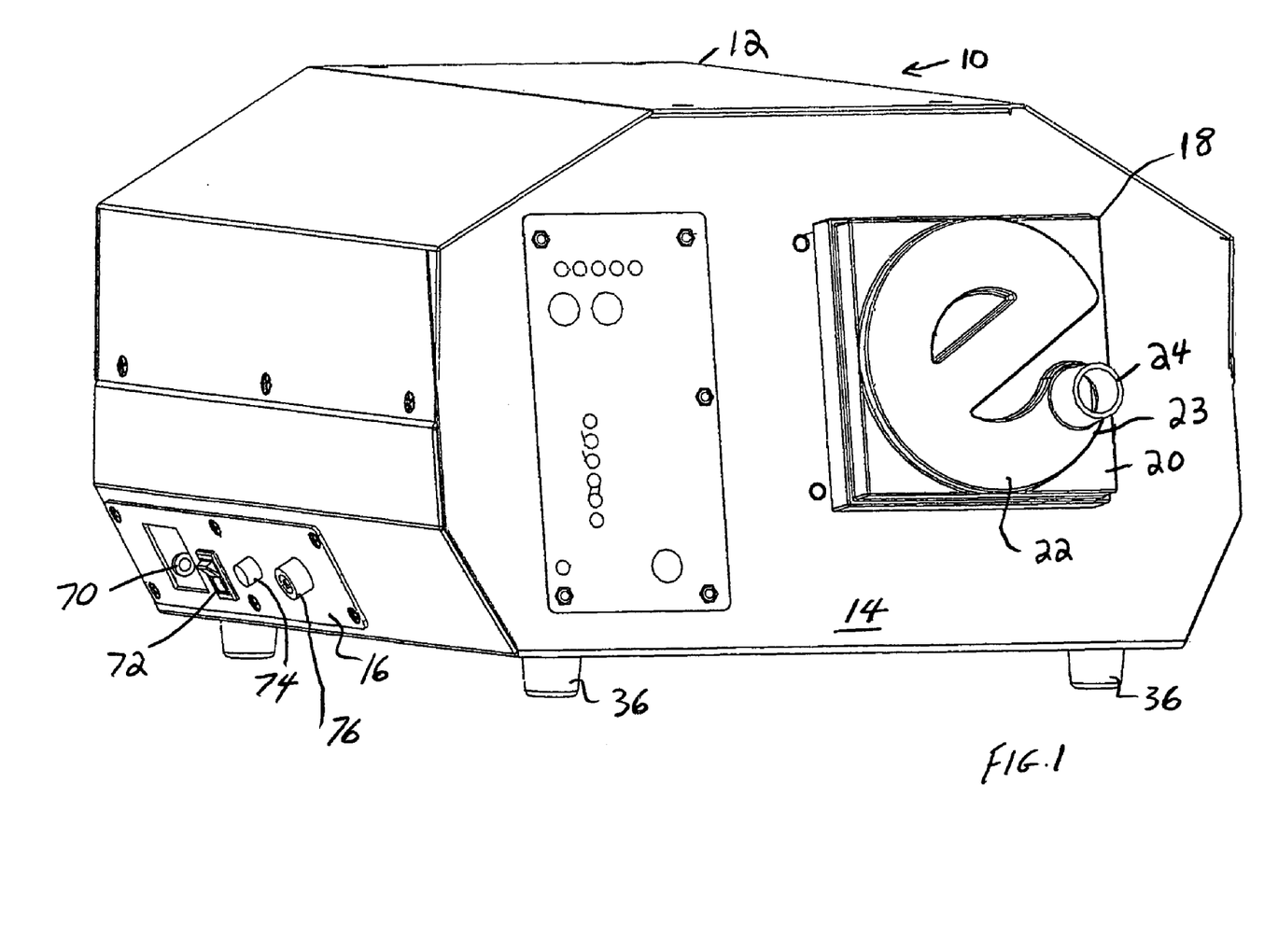
FIG. 1 is a perspective view of one form of the surgical smoke evacuation apparatus of the invention.
Figure 3:
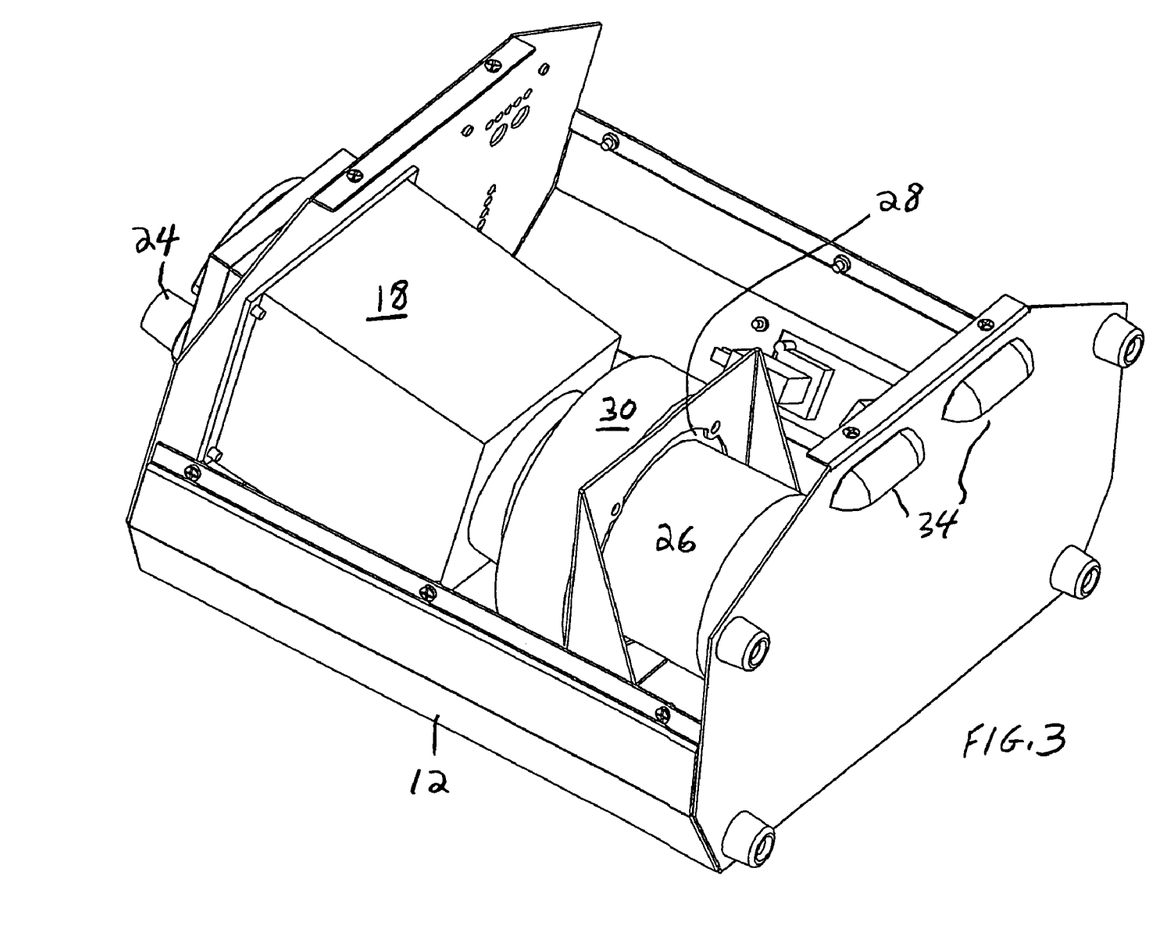
FIG. 3 is an interior perspective view of the smoke evacuation apparatus of FIG. 1 with the top removed.

The apparatus of the invention, a preferred embodiment 10 of which is illustrated in FIG. 1, comprises a main housing 12 that provides a main control panel 14 on the front side and an auxiliary control panel 16 on the left side. At the right side of the front panel is mounted a removable filter assembly 18 according to the invention, more details of which are provided below. The front 20 of the filter assembly projects forwardly from the housing and is configured with a symbol 22, in this case a tilted or angled lower case "e" in Helvetica font. The "e" represents or symbolizes the source of the apparatus or supplier, which in this case is the first letter of the Ellman name which is part of the company name which supplies the system previously described. Where the bottom part of the "e" ends 23 is mounted an air inlet 24 or connector for removably receiving the hose connector typically mounted at the end of a plastic vacuum hose 25 as illustrated schematically in FIG. 5. The mounting of the hose connector at the end of the symbol avoids visual obstruction of the displayed symbol. Inside the housing 12 (see FIG. 3) is provided for example a brushless DC blower motor 26 available commercially from many suppliers and having in this case an enlarged air inlet 28 coupled by way of a simple tubular adapter 30 to the perforated rear 32 (FIG. 5) of the filter assembly. Two louvers acting as air outlets 34 for the filtered air are at the rear. In operation, an internal 2-stage fan (the details of which are not shown) develops a suitable suction at the air inlet 24 by discharging a powerful stream of air at its outlet 34. The discharged air exits the housing via a muffler (not shown) and a sound-deadening mesh (not shown) over the louvers 34. Standoffs 36 isolate the unit from its support. The speed of the motor 26 may be controlled in a known manner. Typically, the suction generated is inversely proportional to the air flow rate.

The vacuum hose 25 is connected at one end to the housing air inlet 24. In the referenced patent U.S. Pat. No. 6,001,077, the hose is connected in-line to an external pre-filter, followed by a charcoal filter inside the housing. While it is possible to include both these filter components inside the removable cartridge 18, in accordance with the present invention, for improved and safer filtering action it is preferred that a six components system be employed comprising, in the order named:

a prefilter 38 whose function is to trap and remove gross particulate and casual fluid;

a viral paper filter 40 capable of filtering extremely small micro-organisms, and is also available commercially from many suppliers. The filter described in U.S. Pat. No. 5,874, 052 may be one example of such a suitable filter for capturing particulates and micro-organisms;

a porous membrane 42 to retain charcoal particulates from the downstream filter component 44;

an activated carbon filter 44 for the removal and adsorption of odors and toxic gases produced by burning tissues;

another porous membrane 46 to retain charcoal particulates from the upstream filter component 44;

an expanded foam and paper media 48 used to trap activated carbon particles from migrating out of the upstream carbon filter 44.

Downstream of and immediately following the removable cartridge 18 is the duct 30 having an inlet opening configured to substantially match the outlet at the perforated rear panel 32 from the generally rectangular or square outlet of the removable cartridge, and having an outlet opening configured to substantially match the inlet of the suction motor 26. The air flow through the filter is indicated by the arrow 50 in FIG. 6.

Figures 4, 5:
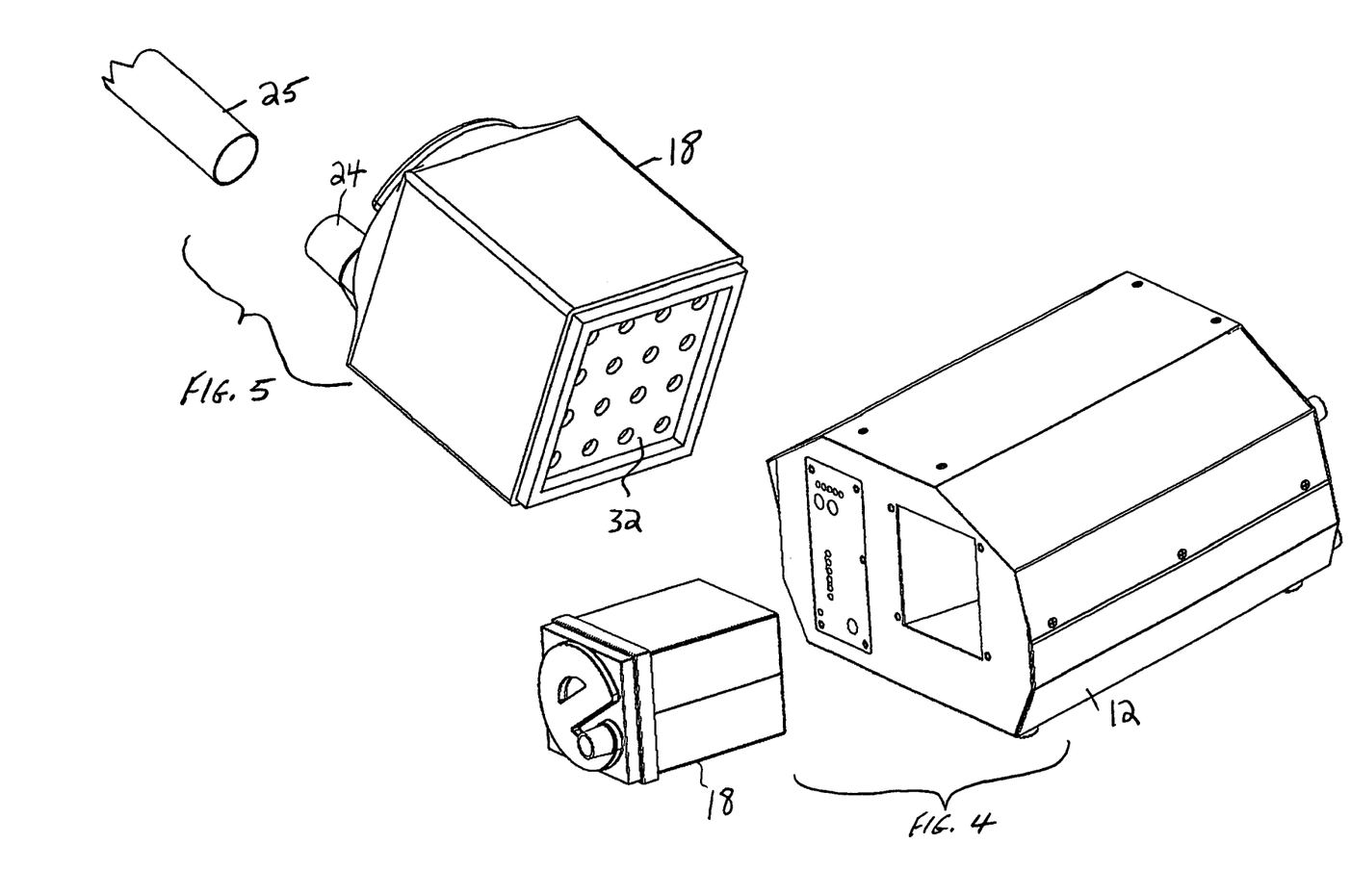
FIG. 4 is a view similar to that of FIG. 1 but showing the filter assembly separated from the housing.
FIG. 5 is an enlarged rear perspective view of the filter assembly of FIG. 3, also showing the end of a hose that would in use be connected to the connector at the front of the filter assembly.

FIG. 5 is a rear view of the filter 18 and shows schematically the end of the hose (sometimes referred to as a wand) 25 to be mounted on the inlet 24 of the filter during use.

As mentioned, a feature of the invention is to locate a 3-D symbol 22 representing the source of the apparatus and positioning the wand or hose inlet 24 at an end 23 of the symbol to promote product/source identification, as well as indicate the filter removal location. The 3-D projecting symbol can also be used by the user to pull out the filter 18 when it needs replacement. FIGS. 7-12 illustrate variations to improve the functioning of the symbol 22 as a handle for replacing the filter.

Figure 7:
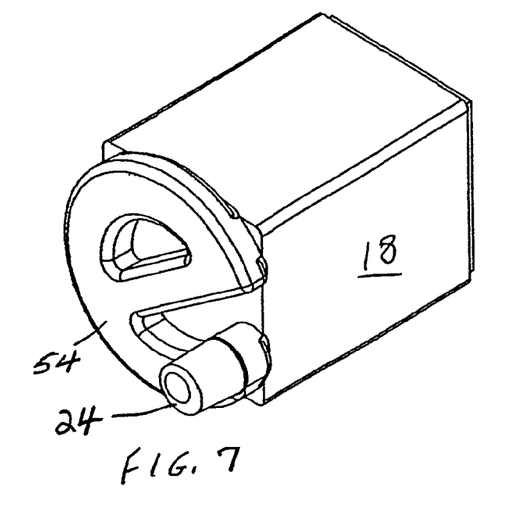
FIG. 7 is a perspective view of a modification of the filter assembly of FIG. 4.
Figure 8:
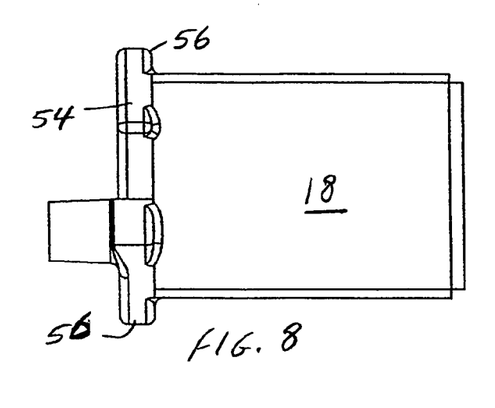
FIG. 8 is a side view of the modification of FIG. 7.
Figures 9, 11, 12:
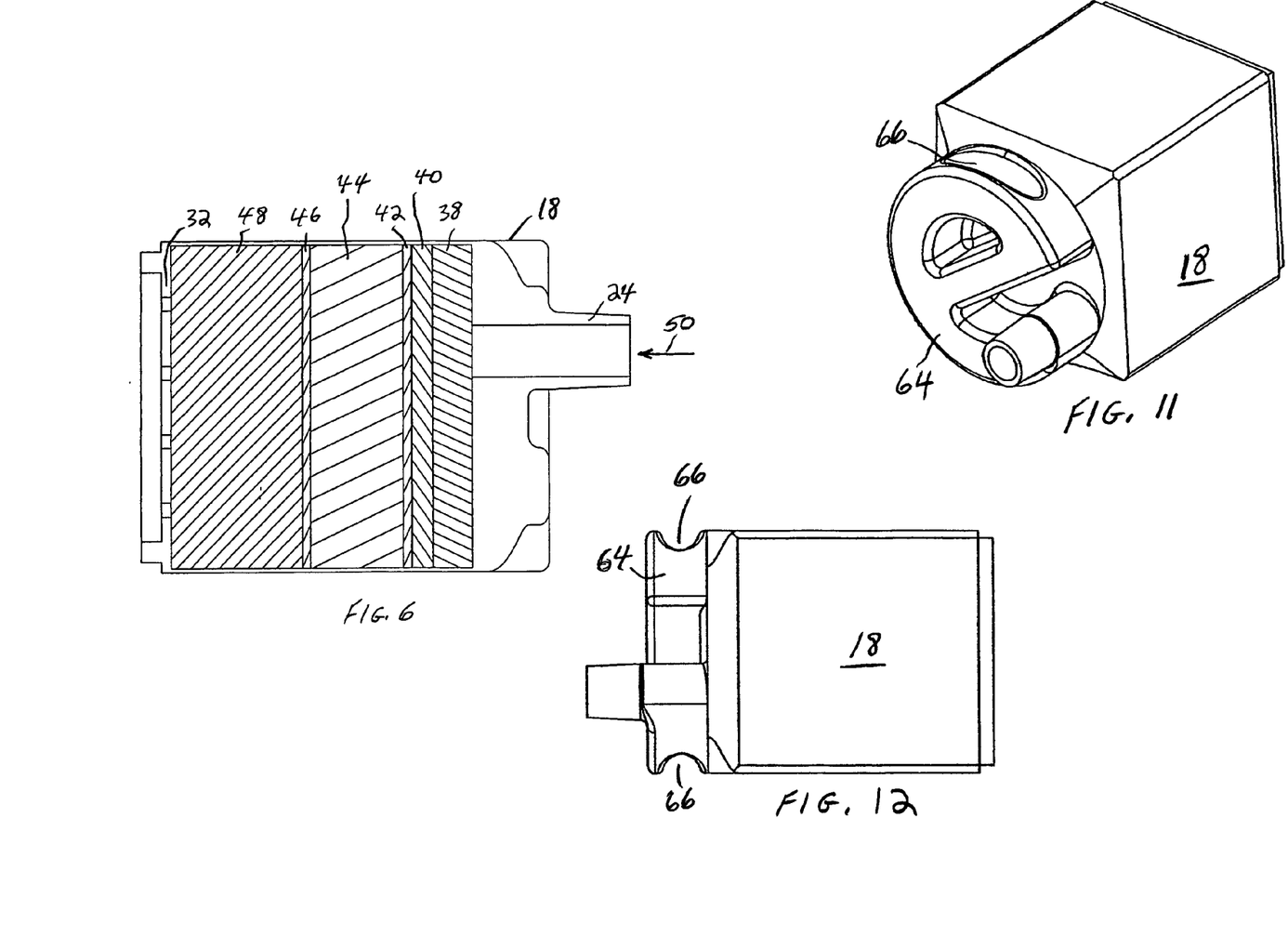
FIG. 9 is a front view of the modification of FIG. 7
FIG. 11 is a perspective view of a further modification of the filter assembly of FIG. 4.
FIG. 12 is a side view of the modification of FIG. 11.
Figure 9:
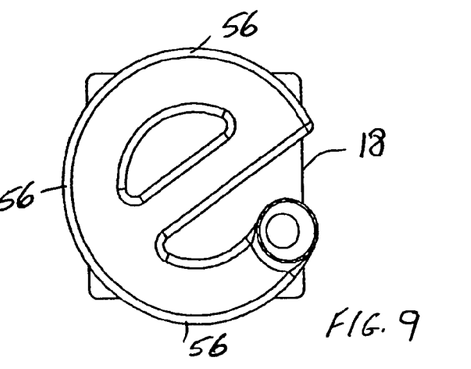

In the first modification of FIGS. 7-9, the symbol 54 is enlarged relative to the filter housing so that at least two edges extend externally of the housing, indicated at 56.

Figure 10:
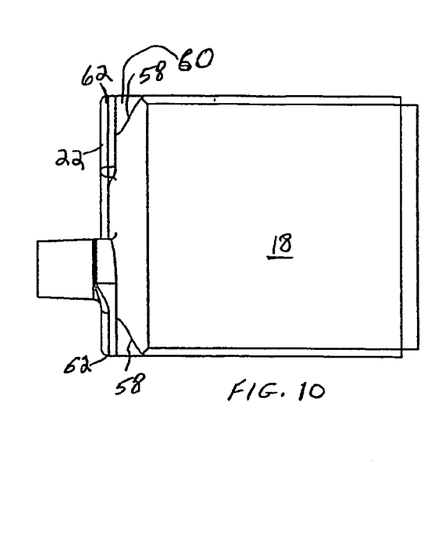
FIG. 10 is a side view of a further modification of the filter assembly of FIG. 4.

In the second modification of FIG. 10, the symbol 22 is unchanged relative to the filter housing but the adjacent end 58 of the filter housing is recessed 60 so that at least two edges of the symbol are usable as a handle, indicated at 62.

In the third modification of FIGS. 11-12, the symbol 64 is thickened and at least two opposed regions of the thickened symbol are recessed 66 to form a handle or grip for easy removal of the filter. Other variations for easier removal of the filter will be evident to those skilled in this art.

The controls for operating the apparatus include on a panel 16 (FIGS. 1 and 13) on the left, starting from the left side, a socket 70 for an AC cable, a manual main on-off switch 72, a connector 74 for an external footswitch 75 for electrical on-off operation of the unit, and a connector 76 for an external footswitch 77 for pneumatic on-off operation of the unit.

Figure 2:
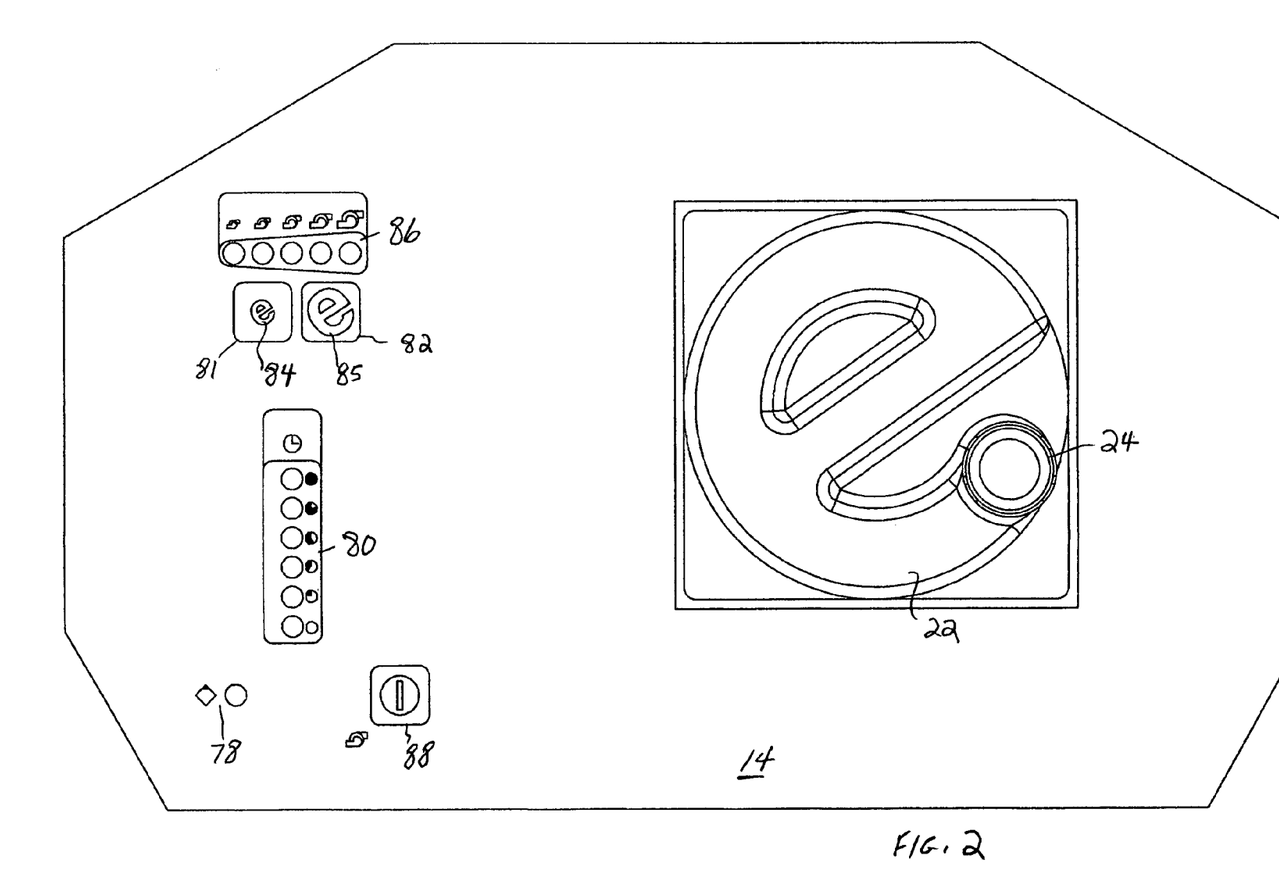
FIG. 2 is an enlarged front schematic view of the front panel showing its controls and indicators.

On the front panel 14 (FIG. 2) are controls and indicators including:

service light indicators 78 warning of a filter replacement;

an indicator 80 with a column of lights indicating how much time left before replacement of the filter;

two buttons 81, 82, the one with the smaller tilted symbol 84 for decreasing the suction motor speed and the adjacent one with the larger tilted symbol 85 (both symbols being the same as that 22 on the filter) for increasing the suction motor speed, the actual motor speed being indicated above by a horizontal row 86 of lights.

A suction motor 88 on-off switch is located at the bottom.

Figure 13:
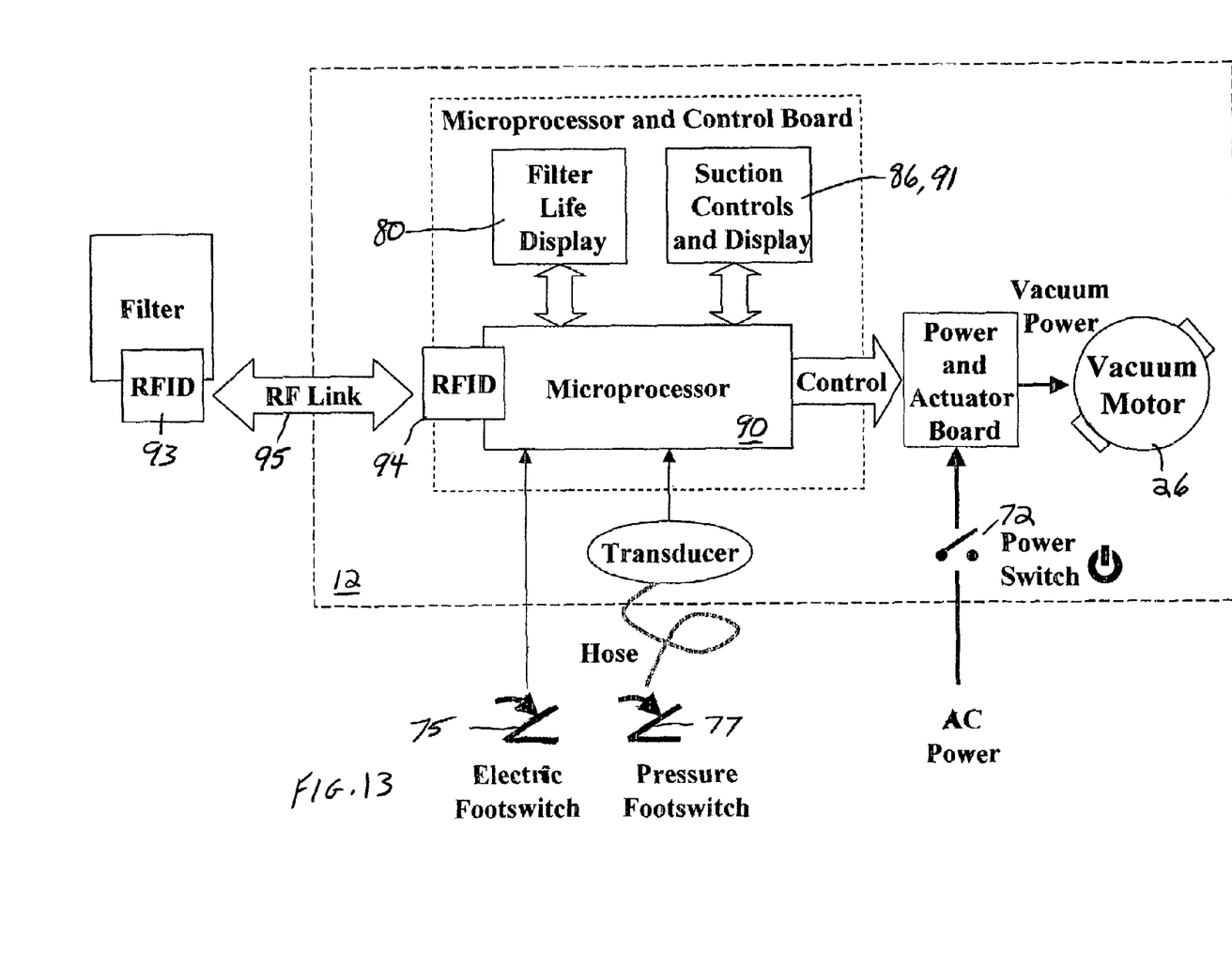
FIG. 13 is a schematic block diagram of the apparatus electronics to provide the functions described below, illustrating the connections between the various system components and the controls and indicators on the front panel.

FIG. 13 illustrates one possible schematic electrical circuit for the unit. A microprocessor 90 controls the operation. Input signals arrive from the external controls 75, 77, and from the internal suction control 91. These signals are processed and output signals are passed on to the displays 80, 86 and to the motor 26.

As a further improvement in automating the filter life indicators, optionally a conventional radio-frequency identifier tag (RFID) may be added to the filter, indicated by 93, and a companion RFID unit 94 inside the housing and electrically connected to the microprocessor 90. These tags are commercially available and communicate by way if an RF link 95. The RFID tag 93 on the filter generates a coded message that informs the microprocessor 90 that the filter 18 is appropriate for the apparatus and a filter approved by the supplier to maintain warranties. The microprocessor 90 can be programmed to disable operation without an approved filter in place to ensure that safe filtered air is outputted from the apparatus. The filter life indicators (typically hours of use) are controlled by the number of times the apparatus has been switched on and the duration of the use. The use is monitored by an electronic timer in the microprocessor 90.

An effective surgical smoke evacuator uses a high flow and intake velocity to capture the smoke with the wand, draw it through the hose, pass it through the filter to remove all unsafe or odorous elements, and recirculate the processed back into the operating room. The user-friendly apparatus of the invention performs these tasks efficiently and safely. It efficiently removes smoke from a surgical operatory area for better visibility, protects a medical team from smoke plume containing viruses, eliminates for the most part unpleasant smoke and odors, and also draws cool air over the surgical site.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. Apparatus for smoke or plume evacuation arising from operation of laser-surgical, electrosurgical, radiosurgical, and electrocautery devices, comprising:
   a) a housing having a front panel,
   b) a removable filter cartridge mounted inside the housing, the filter cartridge having a front panel accessible on the housing front panel and having an exposed air inlet at the housing front panel and an air outlet inside the housing, the filter cartridge being removable from the housing via the housing front panel,
   c) a motor in the housing and connected to the filter cartridge air outlet for forcing air at the air inlet to flow through the filter and to establish a suction at the air inlet,
   d) the filter cartridge air inlet being adapted to receive a removable vacuum hose whereby any air in the hose which may contain smoke or plume is forced through the filter when the apparatus is activated,
   e) the filter cartridge containing viral-trapping and odor-removing filter sections positioned such that the air from the air inlet is forced through said sections.

2. Apparatus for smoke or plume evacuation as claimed in claim 1, wherein the filter comprises a viral-trapping component and a charcoal component.

3. Apparatus for smoke or plume evacuation as claimed in claim 2, wherein the filter further comprises charcoal trapping components flanking the charcoal component.

4. Apparatus for smoke or plume evacuation as claimed in claim 1, wherein the filter has on the filter's front panel a symbol indicative of the source of the apparatus.

5. Apparatus for smoke or plume evacuation as claimed in claim 4, wherein the filter air inlet is mounted on the symbol indicative of the source of the apparatus.

6. Apparatus for smoke or plume evacuation as claimed in claim 5, wherein the symbol is raised above the filter's front panel to form a 3-D configuration.

7. Apparatus for smoke or plume evacuation as claimed in claim 5, wherein the symbol comprises a lower case letter and the filter air inlet is mounted on an end of the lower case letter.

8. Apparatus for smoke or plume evacuation as claimed in claim 7, wherein the lower case letter is tilted.

9. Apparatus for smoke or plume evacuation as claimed in claim 6, wherein the symbol is the letter e in Helvetica font.

10. Apparatus for smoke or plume evacuation as claimed in claim 5, wherein a handle region for removing the filter cartridge is provided behind the symbol.

11. Apparatus for smoke or plume evacuation as claimed in claim 10, wherein the handle region is formed by enlarging the symbol to extend laterally beyond the filter cartridge.

12. Apparatus for smoke or plume evacuation as claimed in claim 10, wherein the handle region is formed by thickening the symbol and forming a recess at the symbol edge.

13. Apparatus for smoke or plume evacuation as claimed in claim 10, wherein the handle region is formed by providing a recessed area in the filter just behind the symbol.

14. Apparatus for smoke or plume evacuation as claimed in claim 1, further comprising indicator means on the apparatus front panel to indicate suction power and filter life.

15. Apparatus for smoke or plume evacuation as claimed in claim 14, further comprising means inside the apparatus housing and comprising circuits connected to the indicator means and to the motor and to a timer of apparatus use.

16. Apparatus for smoke or plume evacuation as claimed in claim 14, further comprising an RFID tag on the filter cartridge and circuit means connected to the RFID tag for controlling operation of the apparatus.

17. Apparatus for smoke or plume evacuation as claimed in claim 1, wherein the filter cartridge comprises in the order named starting from the front panel:
   a prefilter to trap and remove gross particulate and casual fluid,
   a viral paper filter capable of filtering extremely small micro-organisms,
   a first porous membrane to retain charcoal particulates from the downstream filter component,
   an activated carbon filter for the removal and adsorption of odors and toxic gases produced by burning tissues,
   a second porous membrane to retain charcoal particulates from the upstream filter component,
   an expanded foam and paper media to trap activated carbon particles from migrating out of the upstream carbon filter.

* * * * *